US008372001B2

(12) United States Patent
Akagi

(10) Patent No.: US 8,372,001 B2
(45) Date of Patent: Feb. 12, 2013

(54) PORTABLE ELECTRONIC DEVICE AND CAPSULE ENDOSCOPE DIAGNOSIS SYSTEM

(75) Inventor: Toshimasa Akagi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1328 days.

(21) Appl. No.: 11/662,028

(22) PCT Filed: Jan. 20, 2006

(86) PCT No.: PCT/JP2006/300845
§ 371 (c)(1),
(2), (4) Date: Apr. 9, 2007

(87) PCT Pub. No.: WO2006/087885
PCT Pub. Date: Aug. 24, 2006

(65) Prior Publication Data
US 2008/0033248 A1    Feb. 7, 2008

(30) Foreign Application Priority Data
Feb. 17, 2005  (JP) .................. 2005-040949

(51) Int. Cl.
*A61B 1/04* (2006.01)
*H01M 2/10* (2006.01)
*G06F 1/16* (2006.01)
*H05K 5/00* (2006.01)
*H05K 7/00* (2006.01)

(52) U.S. Cl. .............. 600/109; 429/100; 361/679.57

(58) Field of Classification Search ......... 429/96–100; 361/798, 600, 601
See application file for complete search history.

(56) References Cited

U.S. PATENT DOCUMENTS

| 3,186,878 | A | * | 6/1965 | Filander | 429/97 |
| 4,031,295 | A | * | 6/1977 | Rigazio | 429/100 |
| 4,138,531 | A | * | 2/1979 | Thompson | 429/98 |
| 5,229,220 | A | * | 7/1993 | Stanton et al. | 429/1 |

(Continued)

FOREIGN PATENT DOCUMENTS

| JP | 50-34029 | 4/1975 |
| JP | 56-16761 | 4/1981 |

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

The present invention is directed to reliably prevent a trouble that a battery is loaded either in a state where a ribbon is entirely housed in a battery housing or without a ribbon by a simple method using a ribbon. Guide parts (83, 84) are provided on both side walls (57, 58) of a battery housing (53). A ribbon (81) is set so as to cross the battery housing (53) in a stretched state by the guide parts (83, 84) in a position where the battery can be taken out by drawing the ribbon (81). With the configuration, at the time of loading a battery, by making the ribbon (81) extend outside, the ribbon (81) is not entirely housed in the battery housing (53) or absence of the ribbon (81) in the battery housing (53) can be prevented. By making the battery front end face come into contact with the stretched ribbon (81) and inserting a battery, a normal loading state in which the ribbon (81) is pushed to the deepest place can be assured. The battery ejecting function with a simple ribbon (81) can be reliably displayed.

12 Claims, 12 Drawing Sheets

U.S. PATENT DOCUMENTS

| | | | | |
|---|---|---|---|---|
| 5,308,717 | A | * | 5/1994 | Gordin ............................ 429/99 |
| 5,413,499 | A | * | 5/1995 | Wright et al. ................. 439/500 |
| 5,436,088 | A | * | 7/1995 | Castaneda et al. .............. 429/96 |
| 5,437,938 | A | * | 8/1995 | Mitsui et al. ...................... 429/1 |
| 5,508,123 | A | * | 4/1996 | Fan ................................. 429/96 |
| 5,601,939 | A | * | 2/1997 | Zander ........................... 429/98 |
| 5,728,486 | A | * | 3/1998 | Tamaru .......................... 429/97 |
| 5,905,632 | A | * | 5/1999 | Seto et al. ................. 361/679.55 |
| 6,302,454 | B1 | * | 10/2001 | Tsurumaru et al. ........... 292/175 |
| 6,796,819 | B2 | * | 9/2004 | Chen et al. .................... 439/160 |
| 2004/0076858 | A1 | * | 4/2004 | Bartholf et al. ................... 429/1 |
| 2004/0225223 | A1 | | 11/2004 | Honda et al. |
| 2004/0233630 | A1 | * | 11/2004 | Imamura ....................... 361/686 |
| 2005/0288557 | A1 | * | 12/2005 | Yokoi et al. ................... 600/176 |

FOREIGN PATENT DOCUMENTS

| | | |
|---|---|---|
| JP | 3-77265 | 4/1991 |
| JP | 5-234575 | 9/1993 |
| JP | 5-343040 | 12/1993 |
| JP | 9-107588 | 4/1997 |
| JP | 9-320560 | 12/1997 |
| JP | 2000-48790 | 2/2000 |
| JP | 2002-42754 | 2/2002 |
| JP | 2003-31195 | 1/2003 |
| JP | 2004-39598 | 2/2004 |
| JP | 2004-337596 | 12/2004 |

* cited by examiner

PORTABLE ELECTRONIC DEVICE AND CAPSULE ENDOSCOPE DIAGNOSIS SYSTEM

TECHNICAL FIELD

The present invention relates to a portable electronic device and a capsule endoscope diagnosis system.

BACKGROUND ART

Generally, in various portable electronic devices, a battery as a power source has to be exchangeably loaded. As a well-known technique, there is a portable electronic device having a configuration such that a battery is loaded so as to be placed on a ribbon whose one end is fixed and which is arranged in a battery housing and, at the time of exchanging the battery, the battery is taken out from the battery housing by drawing a free end of the ribbon. The configuration is employed because the ribbon constructed by a bias fabric made of polyester fibers or the like has high tensile stress, and both ends of the ribbon do not fray.

However, such a configuration has a drawback. In the case where the battery is loaded in a state where the ribbon is placed in an unexpected position such as a buried state where the whole ribbon including the free end side is placed in the battery housing or an empty state where the whole ribbon is placed in a position out of the battery housing, the ribbon does not function and the battery cannot be taken out. There have been a number of proposals for solving the drawback. As an example, a technique of fixing a free end of a ribbon to the cover of a battery housing has been proposed (refer to, for example, Patent Document 1). There are also proposals of a battery ejecting structure requiring no ribbon in place of the method using a ribbon having the above-described drawback (refer to, for example, Patent Documents 2 to 6). Further, there are also products each having an ejecting mechanism of ejecting a battery from a battery housing when an ejection button is depressed.

Patent Document 1: Japanese Patent Application Laid-Open No. H9-107588
Patent Document 2: Japanese Patent Application Laid-Open No. H5-234575
Patent Document 3: Japanese Patent Application Laid-Open No. H9-320560
Patent Document 4: Japanese Patent Application Laid-Open No. 2000-48790
Patent Document 5: Japanese Patent Application Laid-Open No. 2002-42754
Patent Document 6: Japanese Patent Application Laid-Open No. 2003-31195

DISCLOSURE OF INVENTION

Problem to be Solved by the Invention

However, the technique of Patent Document 1 also has a drawback. The cover is closed in a state where whether the ribbon is sandwiched by the cover or not cannot be recognized. When the cover is placed on the rear face of a wireless remote controller and a battery is loaded by mistake in a state where there is no ribbon in a battery housing, the ribbon is placed on the housed battery, and the battery cannot be taken out.

On the other hand, the techniques of Patent Documents 2 to 6 do not use a method using a simple ribbon, so that there is a drawback that the mechanisms are complicated more than necessary. The eject button method is similar to those techniques. For a normal operation, a strong and complicated mechanism is necessary. The method has a drawback that a necessary space is large. Particularly, in portable electronic devices to which the invention is applied and which require waterproof structure, when the necessary space is large as in the eject button method, the structure is projected, and there is a drawback that it is difficult to obtain the waterproof structure.

The present invention has been achieved in consideration of the above and an object of the invention is to provide a portable electronic device and a capsule endoscope diagnosis system with which, by a simple method using a long member such as a ribbon, a trouble of loading a battery in a state where a long member is entirely housed or without the long member in a batter housing can be prevented reliably.

Means for Solving the Problem

A portable electronic device according to one aspect of the present invention includes a battery housing having, at its one end, an opening to/from which a battery is allowed to be inserted/detached, and in which the battery is detachably housed; a long member whose one end is fixed and which is routed in the battery housing, can be drawn by an operation of drawing the other end, and can be pushed to the deepest place in the insertion direction in the battery housing by an operation of inserting the battery whose battery front end face comes into contact with the long member; and guide parts provided on both side walls of the battery housing and, when the long member is drawn by the drawing operation, making the long member cross the battery housing so as to be stretched in a position where the battery can be taken out.

In the portable electronic device, the guide parts may be provided in positions to make the long member cross the battery housing in a stretched state in a direction orthogonal to the insertion/detachment direction.

In the portable electronic device, the guide parts may be formed as slits which are formed in the side walls and in which the long member is inserted.

In the portable electronic device, as the guide parts, back-side ends of guide members may be used, the guide members being provided along an insertion direction on the side walls and in which the long member is inserted.

The portable electronic device may further include a device-side connector to which a battery-side connector in the batter front end face can be inserted, in the deepest place in the insertion direction of the battery housing, and the guide parts may be provided in positions to set a position of contact with the battery front end face, of the long member in the stretched state so that the long member do not come into contact with the battery-side connector.

The portable electronic device may further include an outlet which is provided near the opening and from which the other end of the long member is insertably drawn to the outside, and a three-dimensional tab, at the other end of the long member, whose entry to the outlet is not limited.

In the portable electronic device, the tab may have a three-dimensional shape larger than a gap between the battery and an inner face of the battery housing and provided in a position where length from the outlet is smaller than length in the insertion direction of the battery in the case where the long member is drawn at the maximum, and in the case where the tab exists in the battery housing, operation of loading the battery to a normal position is disturbed by the tab.

The portable electronic device may further include a cover member capable of closing the opening, and the tab can be housed in a space formed by a rear end face of the battery housed in the battery housing and the cover member.

The portable electronic device may further include a slide drawing mechanism coupled to the other end of the long member and drawing the long member.

The portable electronic device may further include a cover member capable of covering the opening and the slide drawing member.

The portable electronic device may further include an elastic member which is provided on a wall face in the insertion direction orthogonal to both side walls forming the battery housing, has biasing force by which the elastic member fits in a recess formed in an outer face of a loaded battery, and elastically fits in the recess.

The portable electronic device as set may further include a rib which is provided on a wall face in the insertion direction orthogonal to both side walls forming the battery housing and slidably fits in a guide groove formed in an outer face of a battery and parallel with the insertion direction.

In the portable electronic device, the long member may be a band-shaped member.

A capsule endoscope diagnosis system according to another aspect of the present invention includes a capsule endoscope which includes an image capturing unit, an illuminating unit capable of illuminating an image capturing region, and a transmitting unit capable of sending image data captured by the image capturing unit to the outside and can be swallowed by a subject; a detector having an antenna structure attached to the body surface of the subject and receiving image data transmitted from the transmitting unit as a predetermined electric displacement amount; and the portable electronic device according to the present invention, in which a battery is loaded in a battery housing and which is carried by the subject, and records the image data received by the detector.

Effect of the Invention

In the portable electronic device according to the present invention, guide parts are provided on both side walls of a battery housing. A long member is set so as to cross the battery housing in a stretched state by the guide parts in a position where the battery can be taken out by drawing the long member. With the configuration, at the time of loading a battery, by making the long member extend outside, the long member is not entirely housed in the battery housing or absence of the long member in the battery housing can be prevented. By making the battery front end face come into contact with the stretched long member and inserting a battery, a normal loading state in which the long member is pushed to the deepest place can be assured. An effect such that the battery ejecting function with a simple long member can be reliably realized is produced.

EXPLANATIONS OF LETTERS OR NUMERALS

Figure 1:
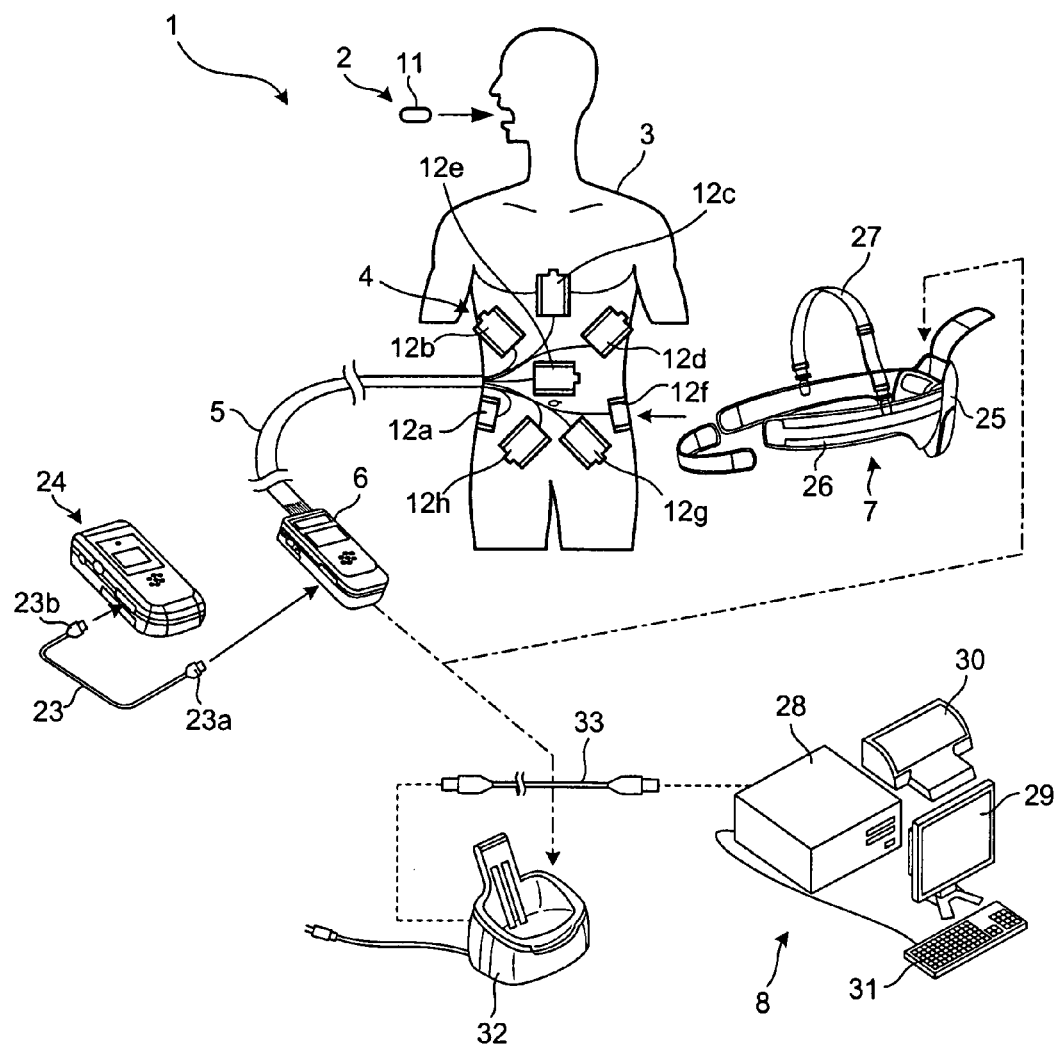
FIG. 1 is a diagram showing a general configuration of a capsule endoscope diagnosis system including a portable receiver according to an embodiment of the present invention.

2 Capsule endoscope
4 Detector
6 Portable receiver (portable electronic device)
20 Battery
21 Battery housing cover (cover member)
42a Battery front end face
42c Battery rear end face
43 Battery-side connector
44 Guide groove
45 Recess
53 Battery housing
53a Opening
56 Bottom face (wall face)
57, 58 Side walls
59 Contact face
71 Device-side connector
72 Rib
73 Elastic retaining piece (elastic member)
81 Ribbon (long member)
83, 84 Slits (guide parts)
85 Slit (outlet)
86 Tab
87 Space
91, 92 Guide members
92a Back-side end (guide)
92b Front-side end (outlet)
93 Outlet
94 Slide drawing mechanism

BEST MODE(S) FOR CARRYING OUT THE INVENTION

Preferred embodiments of the present invention will be described in detail hereinbelow with reference to the appended drawings. An example of applying a portable electronic device of an embodiment to a portable receiver carried by the subject and recording data during diagnosis in a capsule endoscope diagnosis system will be described.

Figure 2:
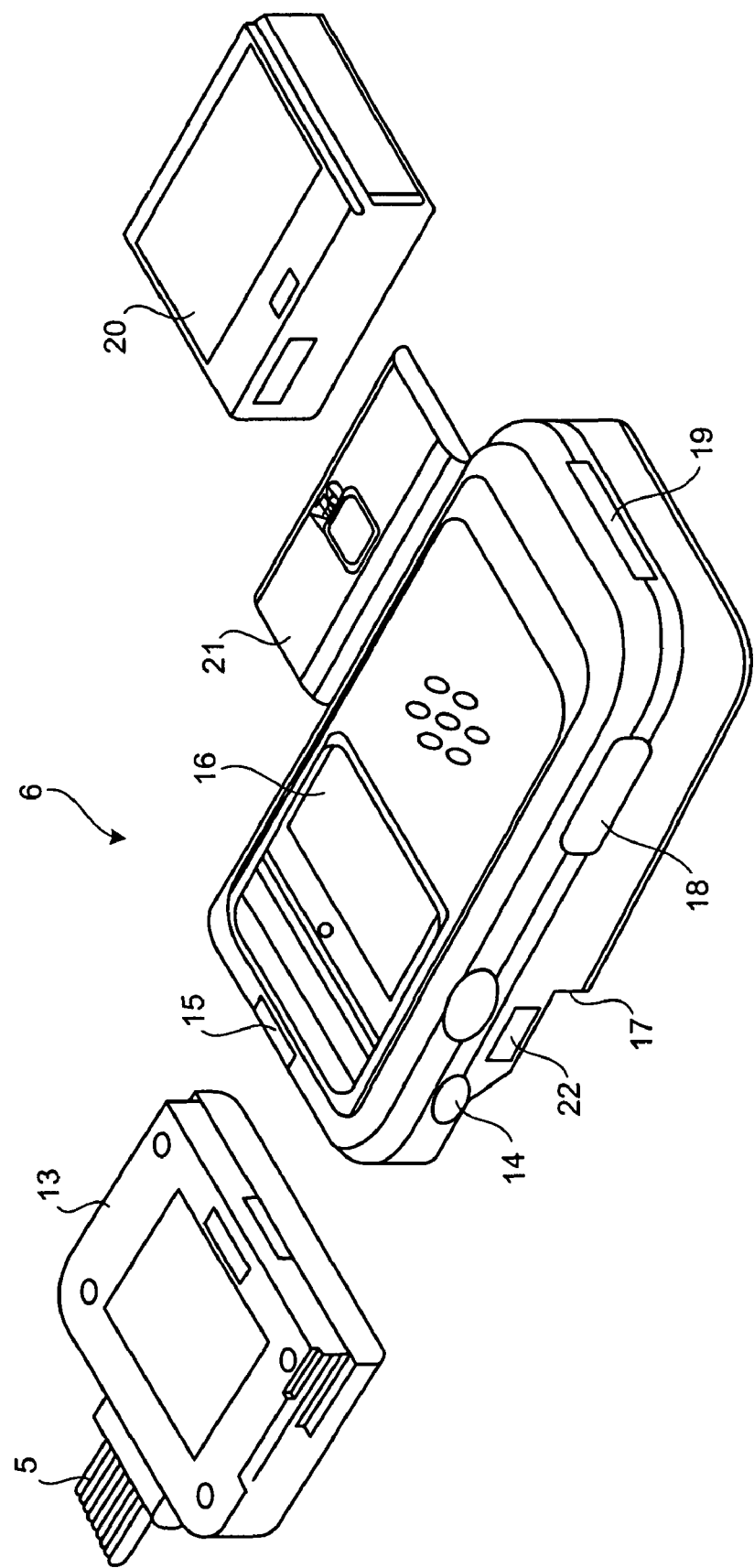
FIG. 2 is a perspective view of an antenna jack and a receiver.

FIG. 1 is a diagram showing a general configuration of a capsule endoscope diagnosis system including a portable receiver according to an embodiment the invention. FIG. 2 is a perspective diagram showing an antenna jack and a receiver. A capsule endoscope diagnosis system 1 is mainly constructed by a capsule endoscope 2, a detector 4 having a loop antenna structure which is directly attached to a predetermined region on the surface of the body of a subject 3 by adhesion or the like, a portable receiver 6 as a portable electronic device electrically connected to the detector 4 via a cable 5 and recording a detection result, a receiver holder 7 attached to the body of the subject 3 and for holding the portable receiver 6 by the body of the subject 3, and an external unit 8 provided on the outside of the subject 3.

A capsule 11 of the capsule endoscope 2 can be swallowed by the subject 3 and has therein an image capturing device, an illuminating device, a signal processing device, a transmitting device, a power source, and the like (which are not shown). The capsule endoscope 2 is swallowed by the subject 3 and introduced into the body cavity. During travel in the body cavity path, the capsule endoscope 2 captures images of an image capture region illuminated by the illuminating device such as an LED by the image capturing device such as a CCD, CMOS, or the like, obtain images of the body cavity, converts the image data to a predetermined signal by the signal processor, and transmits the predetermined signal to the detector 4 by radio waves by the transmitting device.

The detector 4 is a reception antenna for detecting the signal of the image data transmitted by radio waves from the transmitting device in the capsule endoscope 2 as a predetermined electric displacement amount, and is constructed by a plurality of, for example, eight loop antennae 12a to 12h. The loop antennae 12a to 12h are disposed so as to be directly adhered to predetermined regions such as, for example, on the stomach side of the subject 3, right and left flanks, a region around the pit of the stomach, the right and left seventh ribs, and right and left lower stomach regions.

The eight cables 5 extended from the loop antennae 12a to 12h are constructed by, for example, coaxial lines having excellent shielding performance. The length of the cable 5 is preliminarily determined for each of the positions on the body surface of the loop antennae 12a to 12h. The cables 5 are led in to an antenna jack 13 having a rectangular shape in plan view, for electric connection to the portable receiver 6.

The portable receiver 6 has a slightly-flat rectangular parallelepiped shape and includes, as shown in FIG. 2, a power source switch 14, a display lamp 15, a liquid crystal display 16, an antenna unit bay 17, a viewer cable connector 18, a cradle port connector 19 and the like. In the portable receiver 6, circuit members including a CF memory for recording image data transmitted via the cable 5 are mounted on a board, and a battery 20 of capacity which can address a diagnosis for long time of eight to ten hours can be loaded in a battery housing which will be described later. 21 denotes a battery housing cover as a cover member which closes the opening of the battery housing. The antenna unit bay 17 has a connector structure to/from which the antenna jack 13 can be inserted/detached. In the state where the antenna jack 13 is inserted, an internal circuit of the portable receiver 6 and the detector 4 are electrically connected to each other. 22 denotes an eject button for ejecting the antenna jack 13.

The viewer cable connector 18 is provided on the lower end side of one of the side faces of the portable receiver 6. By attaching a connector 23a as one of connectors of a viewer cable 23 to the viewer cable connector 18 and attaching the other connector 23b to a viewer 24, an image for diagnosis to be recorded in the portable receiver 6 can be recognized at any time by the viewer 24.

The receiver holder 7 enables the portable receiver 6 to be held and carried on the body of the subject 3, for example, the left waist part and is constructed by, for example, a pouch 25, a stomach belt 26, a suspender 27, and the like.

The main unit of the external unit 8 is a workstation 28 disposed in, for example, a hospital and has a display 29, a printer 30, a keyboard 31, and the like and, in addition, a cradle 32 for transferring image data recorded on the CF memory in the portable receiver 6 to the workstation 28 at once, and a cradle cable 33 such as a USB cable or the like. When the portable receiver 6 is inserted in the cradle 32 and enters a connection state via the cradle port connector 19, all of the image data recorded on the CF memory in the portable receiver 6 is transmitted to the workstation 28 at once.

Figure 3:
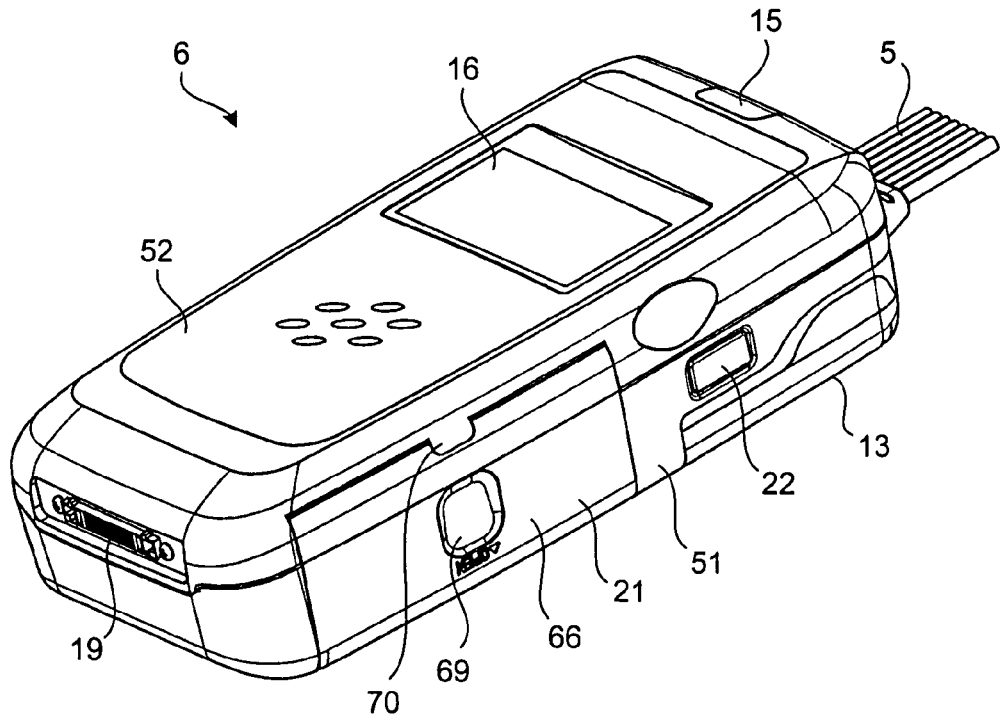
FIG. 3 is a perspective view showing the appearance of a portable receiver 6 in which the antenna jack is loaded.
Figure 4:
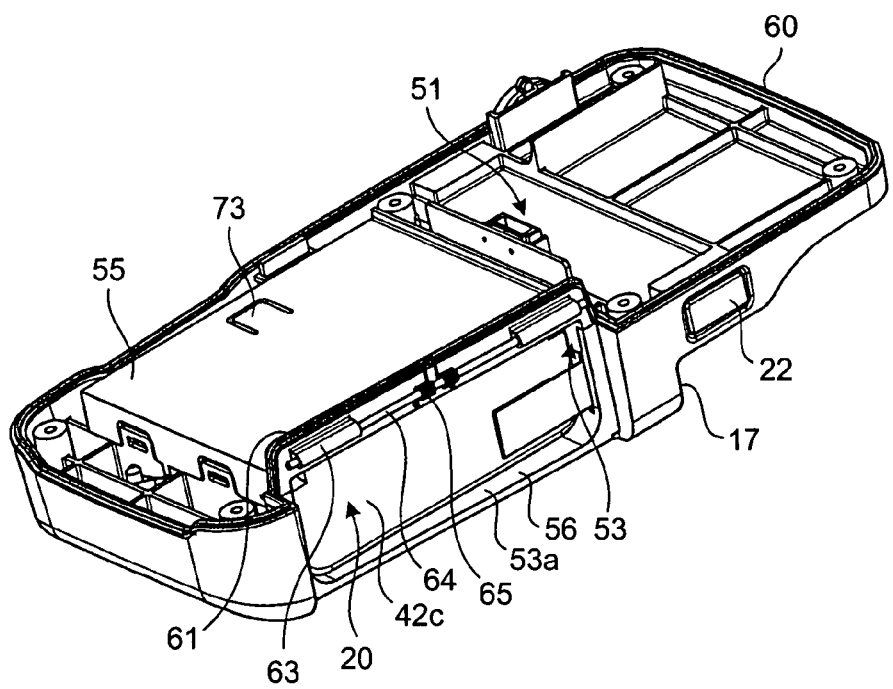
FIG. 4 is a perspective view showing an example of the configuration of a body case side from which a cover case is detached.
Figure 5:
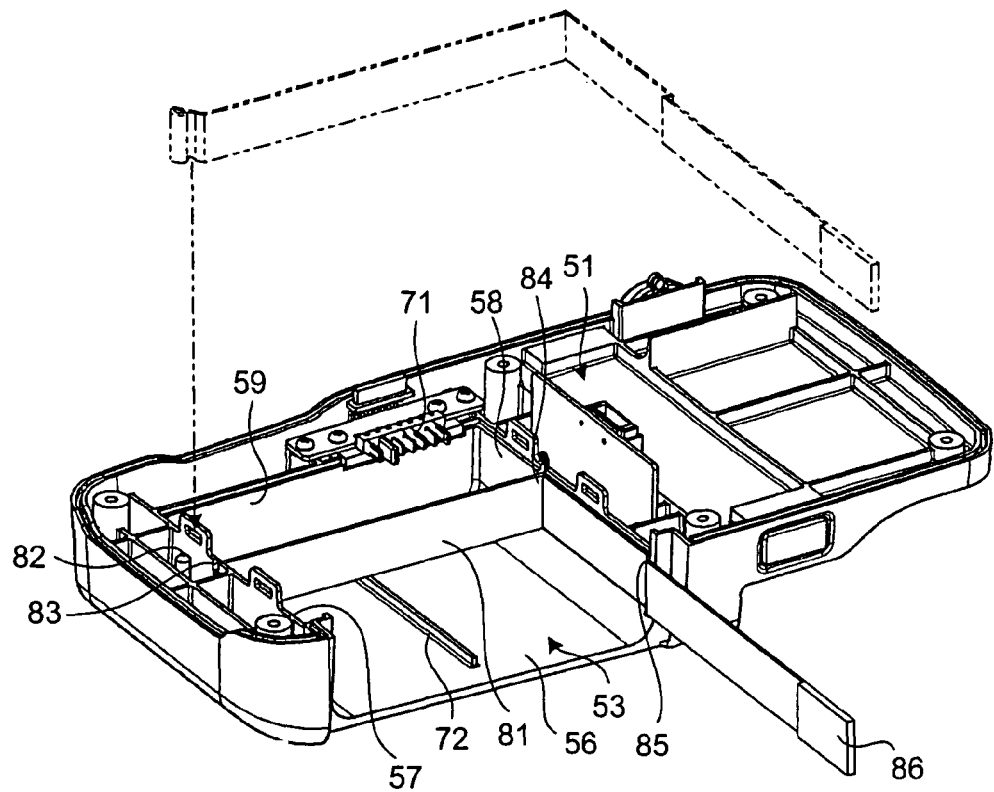
FIG. 5 is a perspective view showing an example of the configuration before a battery is loaded, on the body case side from which a ceiling plate is detached.
Figure 6:
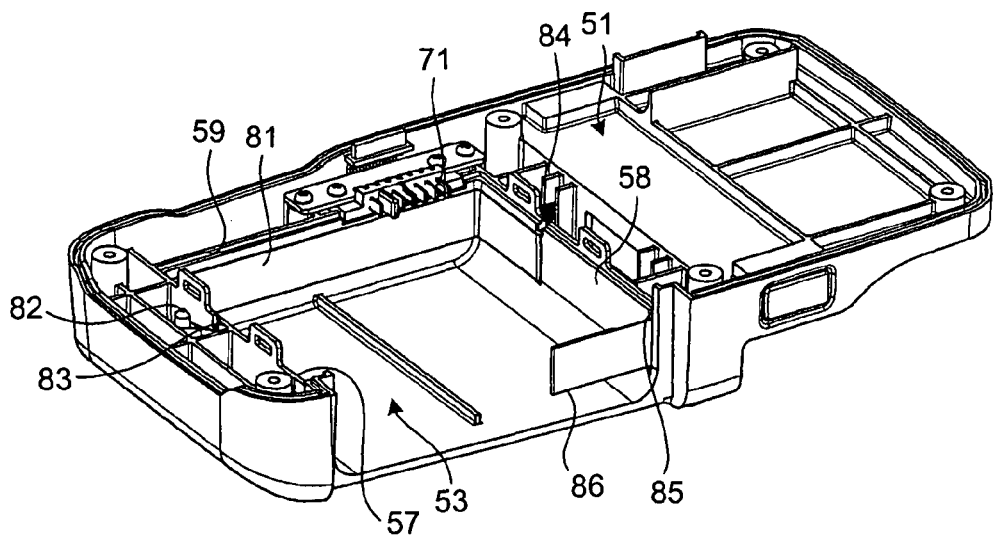
FIG. 6 is a perspective view showing an example of the configuration in a state where the battery (not shown) is loaded, on the body case side from which the ceiling plate is detached.
Figure 7:
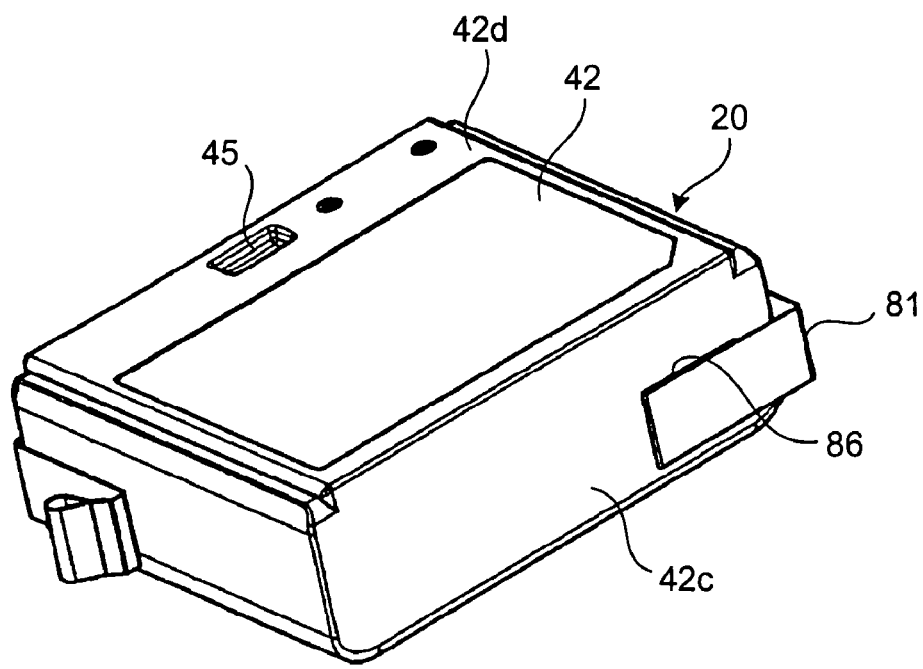
FIG. 7 is a perspective view showing a state where a battery and a ribbon are in a loaded state.
Figure 8:
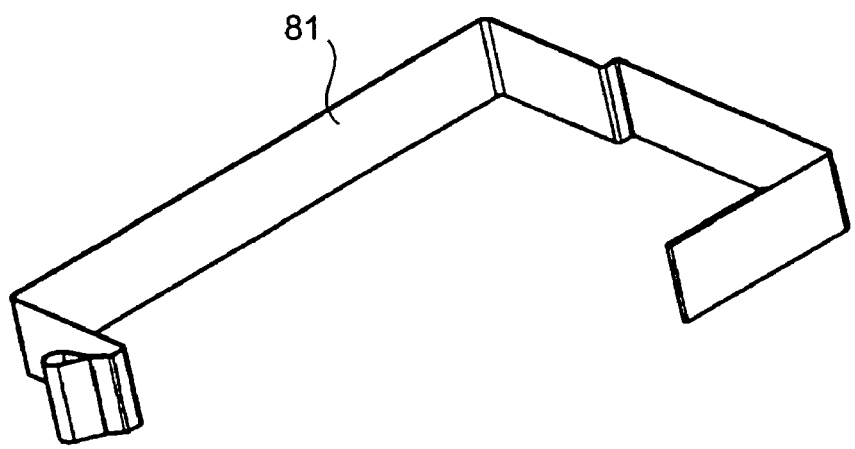
FIG. 8 is a perspective view showing a placing state of the ribbon in the loaded state.
Figure 9:
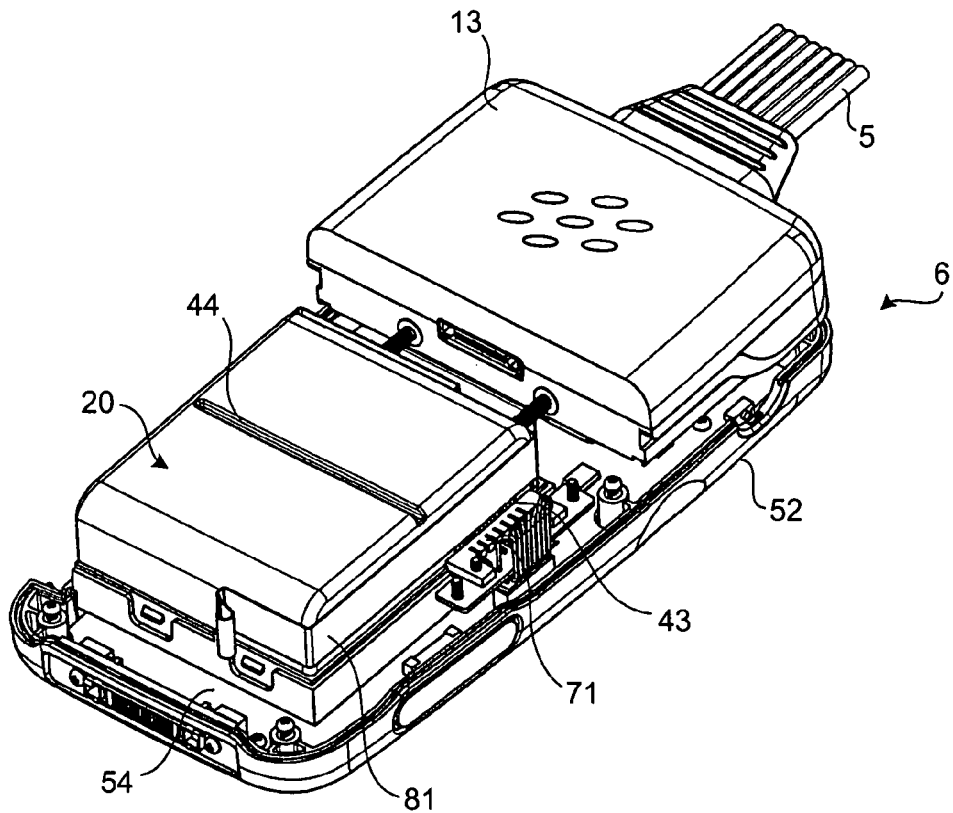
FIG. 9 is a perspective view showing the battery loading state in which the portable receiver 6 is turned over and the body case is not shown.
Figure 10:
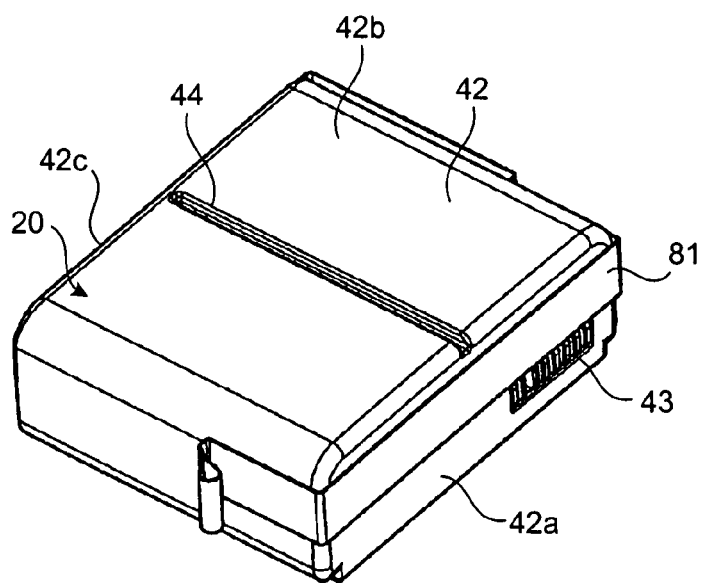
FIG. 10 is a perspective view showing a state where the battery and the ribbon are loaded, seen in the same direction as that of FIG. 9.
Figure 11:
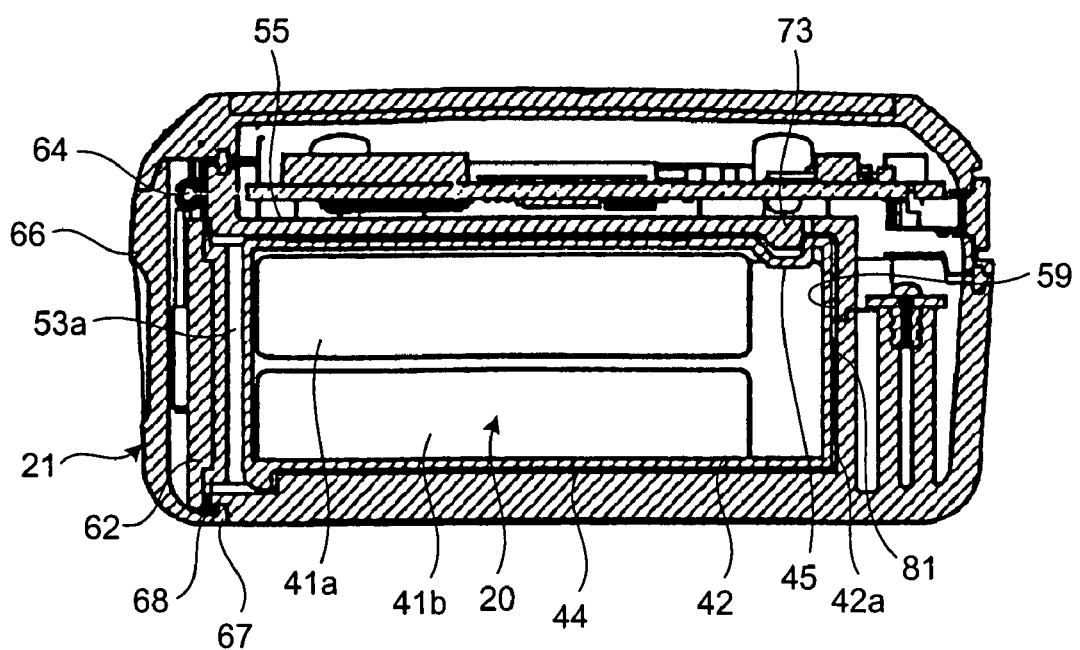
FIG. 11 is a longitudinal rear view of a battery housing in the battery loaded state.
Figure 12:
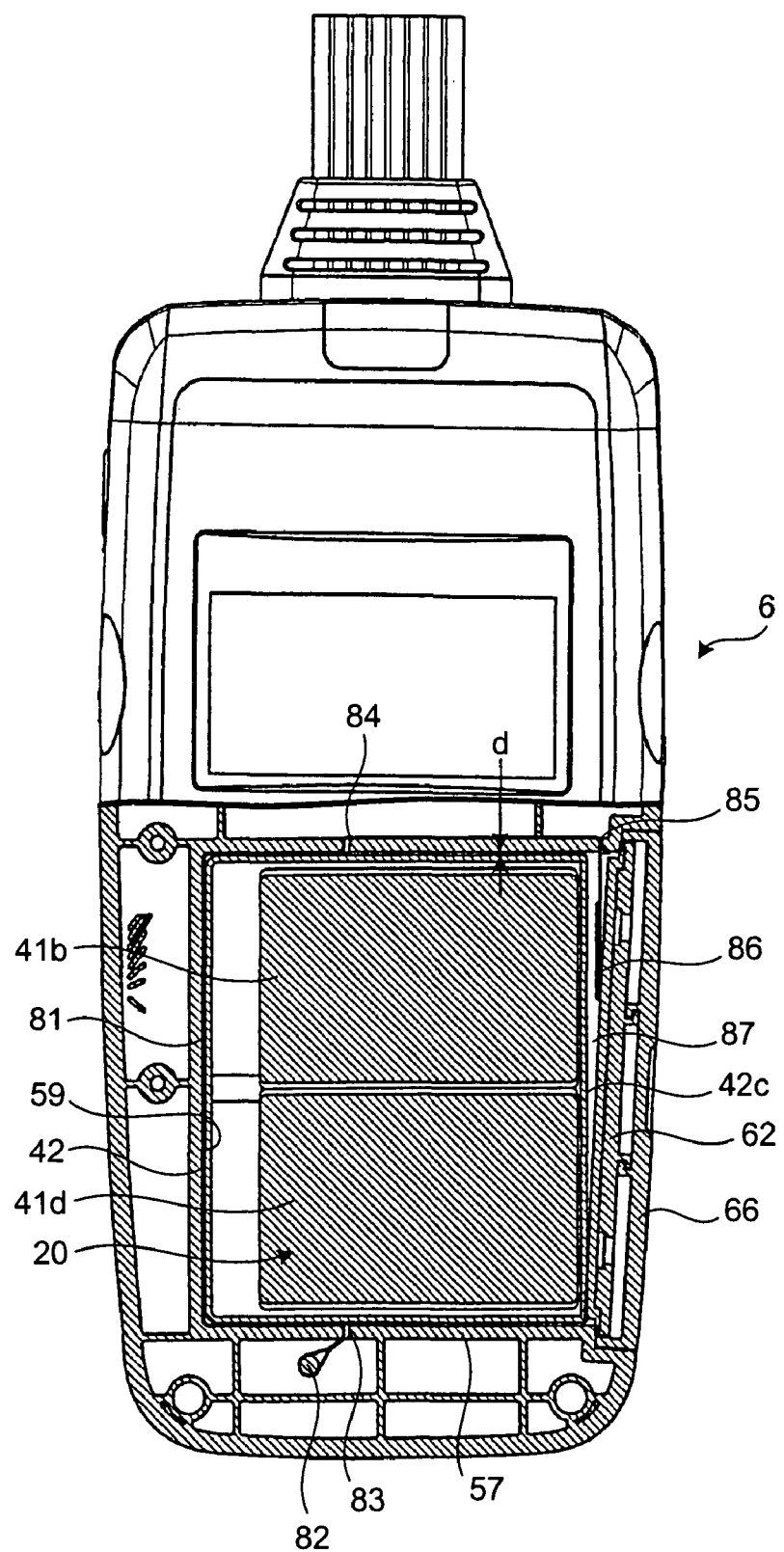
FIG. 12 is a partly-cutaway plan view of the portable receiver 6 in the battery loaded state.
Figure 13:
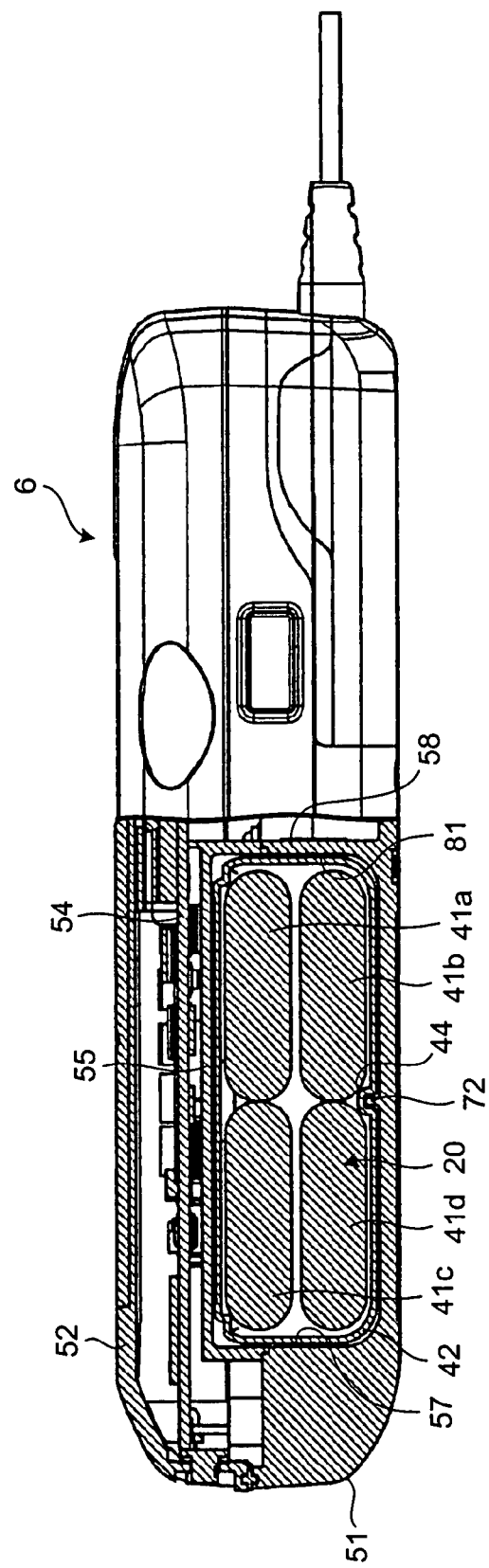
FIG. 13 is a partly-cutaway right side view of the portable receiver 6 in the battery loaded state.

Next, the portable receiver 6 and the battery 20 will be described. FIG. 3 is a perspective view showing the appearance of the portable receiver 6 in which the antenna jack 13 is loaded. FIG. 4 is a perspective view showing an example of the configuration of a body case side from which a cover case is detached. FIG. 5 is a perspective view showing an example of the configuration before a battery is loaded, on the body case side from which a ceiling plate is detached. FIG. 6 is a perspective view showing an example of the configuration in a state where the battery (not shown) is loaded, on the body case side from which the ceiling plate is detached. FIG. 7 is a perspective view showing a state where a battery and a ribbon are in a loaded state. FIG. 8 is a perspective view showing a placing state of the ribbon in the loaded state. FIG. 9 is a perspective view showing the battery loaded state in which the portable receiver 6 is turned over and the body case is not shown. FIG. 10 is a perspective view showing a state where the battery and the ribbon are loaded, seen in the same direction as that of FIG. 9. FIG. 11 is a longitudinal rear view of a battery housing portion in the battery loaded state. FIG. 12 is a partly-cutaway plan view of the portable receiver 6 in the battery loaded state. FIG. 13 is a partly-cutaway right side view of the portable receiver 6 in the battery loaded state.

First, with reference to FIG. 7 and FIGS. 10 to 13, the configuration of the battery 20 loaded in the portable receiver 6 will be described. As described above, the battery 20 has to have capacity capable of addressing diagnosis for eight to ten hours. Two cells each out of four cells 41a to 41d each having a flat cylindrical shape are connected to each other in series, and the two sets are connected in parallel with each other and housed in a pack 42, thereby constructing a lithium ion battery having a rectangular flat shape and having large capacity of 7.4 V and 3600 mA. The battery 20 has, in its battery front end face 42a in the insertion/detachment direction, a battery-side connector 43 having irreversible directivity to loading of the portable receiver 6 and for insertably and electrically connecting to a device-side connector which will be described later. The battery-side connector 43 is provided so as to be shifted in the width and height directions, for example, so as to be in a position corresponding to one cell in the battery front end face 42a. In one of flat faces 42b of the pack 42 forming the outer shape of the battery 20, a guide groove 44 utilizing the gap between built-in cells is formed in parallel with the insertion/detachment direction. The guide groove 44 is formed so as to penetrate on the battery front end face 42a side and so as not to penetrate on a battery rear end face 42c side and is closed. A center position closer to the battery front end face 42a on the other flat face 42d of the pack 42 forming the outer shape of the battery 20, as will be described later, a recess 45 for preventing drop due to its own weight is formed.

Next, the configuration of the portable receiver 6 to which the battery 20 is to be loaded as a power source will be described. As shown in FIG. 3, the portable receiver 6 is constructed by a two-division structure of a body case 51 and a cover case 52 which are made by resin molding or the like. The body case 51 is constructed mainly by a battery housing 53 for detachably housing the battery 20 and the antenna unit bay 17. The cover case 52 is constructed mainly by a board 54 on which circuit members including a CF memory are mounted, and includes the liquid crystal display 16 and the like.

The battery housing 53 is formed in a rectangular shape having, at one end, an opening 53a to/from which the battery 20 is inserted/detached by combining a ceiling plate 55 made by resin molding or the like to a predetermined position of the body case 51. Specifically, in the body case 51, a bottom face 56 as a wall face, first and second side walls 57 and 58 provided upright on the bottom face 56 so as to be parallel with each other, and a contact face 59 provided upright so as to be perpendicular to the bottom face 56 and the first and second side walls 57 and 58 at the deepest part in the insertion/detachment direction are formed in advance in an open state. As shown in FIG. 4, by attaching the ceiling plate 55 onto the first and second side walls 57 and 58 and the contact face 59 so as to be in parallel with the bottom face 56, the battery housing 53 is formed.

In the joint faces of the body case 51, the upstand part of the ceiling plate 55, and the cover case 52, seal grooves 60 and 61 for waterproof that perform sealing by using a packing or the like are formed. Consequently, the portable receiver 6 has the waterproof structure to prevent, for example, erroneous operation of an internal circuit or the like which is wet during medical care in which the portable receiver 6 is carried by the subject 3.

The battery housing cover 21 that closes the opening 53a has a double structure of a waterproof cover 62 and a cover 66. The waterproof cover 62 is formed in the size just fit in the opening 53a and closes the opening 53a. The cover 66 is swingable around a spindle 64, as a swing fulcrum, supported by a support 63 formed at the upstand part of the ceiling plate 55 is biased by a torsion spring 65 in an open direction. The cover 66 is slidably coupled to the waterproof cover 62. Usually, a lock nail 67 formed at the lower end of the cover 66 is retained in a lock groove 68 in the body case 51, thereby maintaining the opening 53a closed with the waterproof cover 62. When a cancel button 69 is operated to push down the cover 66 and retaining of the lock nail 67 is canceled, the cover 66 and the waterproof cover 62 are open by the biasing force of the torsion spring 65. 70 denotes a stopper for regulating the opening state of the cover 66 to an almost horizontal state.

The battery housing 53 is formed in size and shape that the battery 20 is just housed with a very small gap "d" (refer to FIG. 12) between the inner face of the battery housing 53 and the battery 20. The insertion/detachment direction of the battery housing 53 is determined so that the battery 20 is inserted from the right side face of the portable receiver 6. The battery housing 53 has, on the contact face 59 at the deepest part, a device-side connector 71 to which the battery-side connector 43 can be connected. As shown in FIG. 9, the device-side connector 71 is electrically connected to the board 54 side at the position deeper than the battery housing 53.

In the battery housing 53, a rib 72 with which the guide groove 44 formed in the flat face 42b of the pack 42 of the battery 20 slidably engages is provided on the bottom face 56. The rib 72 is not formed near the opening 53a but is formed in a position from some midpoint to the back side in correspondence with the guide groove 44 whose one end is closed.

Further, as shown in FIGS. 4 and 11, the ceiling plate 55 has an elastic retaining piece 73 as an elastic member which is elastically fit in the recess 45 formed in the flat face 42d of the pack 42 in a state where the battery 20 is loaded in the battery housing 53. The elastic retaining piece 73 is formed by cutting a part of the ceiling plate 55 in an almost U shape and usually has a biasing force that fits in the recess 45 on the battery 20 side. When pushed upward, the elastic retaining piece 73 can have a state where it does not fit in the recess 45 against the biasing force.

For the battery housing 53, a ribbon 81 as the long member for taking out the loaded battery 20 is disposed. The ribbon 81 is a band member constructed by a bias fabric made of polyester fibers or the like having properties such that tensile stress is high and both ends of the ribbon do not fray. One end of the ribbon 81 is fixed by being retained by a fixing pin 82 provided upright in a proper position on the outside of the first side wall 57. Basically, one end of the ribbon 81 is fixed and routed so as to pass in the battery housing 53. The ribbon 81 can be pulled by an operation of pulling the other end. By the operation of inserting the battery 20 in a state where the battery front end face 42a is in contact with the ribbon 81, the ribbon 81 can go back to the contact face 59 at the deepest place in the insertion direction in the battery housing 53.

A slit 83 in which the ribbon 81 is inserted is formed in the first side wall 57, and slits 84 and 85 in which the ribbon 81 is inserted are formed in the second side wall 58. The ribbon 81 whose one end is fixed crosses the battery housing 53 by being inserted in the slits 83 and 84 as a guide, goes out from the slit 84, runs on the outside of the second side wall 58, and is inserted in the slit 85. In such a manner, the ribbon 81 is routed and the other end of the ribbon 81 goes out from the opening 53a.

More specifically, as shown in FIG. 5, the slits 83 and 84 are provided in positions to set the ribbon 81 so as to be stretched across the battery housing 53 in a position where the battery 20 is taken out in the case where the other end of the ribbon 81 is pulled at the maximum. In the embodiment, the formation positions of the slits 83 and 84 are positions of equal distances from the contact face 59 and set so that the ribbon 81 extends orthogonal to the insertion direction of the battery 20 and is stretched across the battery housing 53. The formation positions of the slits 83 and 84 are positions ⅓ from the contact face 59 side with respect to the depth of the battery housing 53. In the positions, the elastic retaining piece 73 certainly comes out from the recess 45 on the battery 20 side against the biasing force, and the battery 20 can be sufficiently ejected. The ribbon 81 is inserted from above into the slits 83, 84, and 85 in the body case 51 before division, thereby being routed. By attaching the ceiling plate 55, the ribbon 81 is prevented from coming off upward from the slits 83, 84, and 85.

The ribbon 81 having narrow width which is about ½ of the height (thickness) of the battery front end face 42a is used. The contact positions of the slits 83 and 84 with the battery front end face 42a in the first and second side walls 57 and 58 are set at height positions to set the ribbon 81 so as not be in contact with the battery-side connector 43 as shown in FIG. 10.

The ribbon 81 has a tab 86 used to perform the operation of pulling the ribbon 81, at the end opposite to the free end. The tab 86 has a three-dimensional shape which does not allow insertion to the slit 85 of the tab 86. Although the three-dimensional shape may be larger than the length of the slit 85, the tab 86 in the embodiment is thicker than the width of the slit 85, so that its three-dimensional shape cannot be inserted in the slit 85. The thickness of the tab 86 portion is set to a thickness larger than the gap "d" between the battery 20 and the inner wall of the battery housing 53, so that the tab 86 cannot enter the gap "d". The tab 86 is provided in a position where the length from the slit 85 in the case where the ribbon 81 is pulled at the maximum is shorter than length in the insertion/detachment direction of the battery 20. Concretely, when the ribbon 81 is positioned at the deepest place where it is in contact with the contact face 59, as shown in FIGS. 4, 12, and the like, the tab 86 is positioned slightly out of the slit 85. Consequently, the length from the slit 85 to the tab 86 in the case where the ribbon 81 is drawn at the maximum is length corresponding to the maximum drawing amount. In particular, in the embodiment, when the depth of the battery housing 53 is set as 3a, the length from the contact face 59 to each of the slits 83 and 84 is "a", and the length corresponding to the maximum drawing amount is 2a which corresponds to the length between the slits 84 and 85.

Next, the operation of inserting the battery 20 to the battery housing 53 will be described. After the battery housing cover 21 is opened, the ribbon 81 is drawn at the maximum by holding the tab 86. Since the tab 86 is thicker than the width of the slit 85, a trouble such that the tab 86 enters the body case 51 from the slit 85 before the drawing operation does not occur. When the ribbon 81 is drawn at the maximum, as shown in FIG. 5, the ribbon 81 is stretched so as to cross the battery housing 53 in the direction orthogonal to the insertion/detachment direction due to restriction of the slits 83 and 84. In this state, the ribbon 81 is prevented from being routed by the slits 83 and 84 and the like. Consequently, troubles such that the ribbon does not exist in the battery housing 53 and the whole ribbon 81 enters the battery housing 53 do not occur. In this state, the battery 20 is inserted from the opening 53a side into the battery housing 53.

In this case, the guide groove 44 engages with the rib 72 and slides. When the battery 20 is inserted upside down or from the rear end, the guide groove 44 does not engage with the rib 72 and the battery 20 cannot be inserted, so that the insertion in the opposite direction of the battery 20 can be prevented.

Next, the battery front end face 42a of the inserted battery 20 is made come into contact with the ribbon 81 in the stretched state. Although the contact place is the back side in the battery housing 53 having depth, the ribbon 81 is orderly stretched, so that the operability of the work of making the battery front end face 42a come into contact with the ribbon 81 is high. The battery 20 itself is flat and the battery-side connector 43 is provided on the battery front end face 42a. Consequently, the area of contact with the ribbon 81 is small. However, the contact position of the ribbon 81 in the battery front end face 42a is set according to the height positions of the slits 83 and 84, so that the ribbon 81 can reliably come into contact with the battery-side front end face 42a while avoiding the battery-side connector 43 as shown in FIG. 10 and the like.

After that, when the battery 20 is further pushed, the ribbon 81 also moves to the back side. Finally, in a normal loading position in which the battery-side connector 43 engages with the device-side connector 71 and an electrically connected state is obtained, the ribbon 81 goes to the contact face 59 at the deepest place in a bent shape as shown in FIGS. 6 to 10 and the like while being in contact with the battery front end face 42a. In this case, the ribbon 81 is in contact with the battery front end face 42a in a position in which the ribbon 81 does not overlap the battery-side connector 43, insertion/detachment of the battery-side connector 43 and the device-side connector 71 is not disturbed.

In the state where the battery 20 is loaded, with the inserting operation, the elastic retaining piece 73 of the ceiling plate 55 is retained by the recess 45 in the battery 45, and the battery 20 is prevented from coming off by the biasing force of the elastic retaining piece 73. As a result, even if the opening 53a comes to face downward in a state where the battery 20 is loaded in the battery housing 53, drop due to the own weight of the battery 20 can be prevented.

With the operation of inserting the battery 20, the other end side of the ribbon 81 passes through the slit 85 and is drawn into the body case 51. After completion of the loading of the battery 20, the ribbon 81 and the tab 86 portion on the outside of the slit 85 are put on the battery rear end face 42c and the battery housing cover 21 is closed, thereby enabling the ribbon 81 and the tab 86 portion to be housed in a space 87 by the battery rear end face 42c and the battery housing cover 21 as shown in FIGS. 4, 12, and the like.

The operation of ejecting the loaded battery 20 will now be described. After the battery housing cover 21 is opened, the operation of drawing the ribbon 81 is performed by holding the tab 86 portion. In this case, the ribbon 81 extends so as to cross the battery housing 53 while being in contact with the battery front end face 42a and exists at the deepest place. Therefore, with the operation of drawing the ribbon 81, the battery 20 also is apart from the contact face 59 and moves toward the opening 53a side. The battery 20 is in a state such that the battery-side connector 43 engages with the device-side connector 71 and the drop of the battery 20 is prevented by the retaining between the recess 45 and the elastic retaining piece 73. By the operation of drawing the ribbon 81 stronger than the tensile force, the retained state is canceled, and the battery 20 can be reliably moved in the ejection direction.

Figure 14:
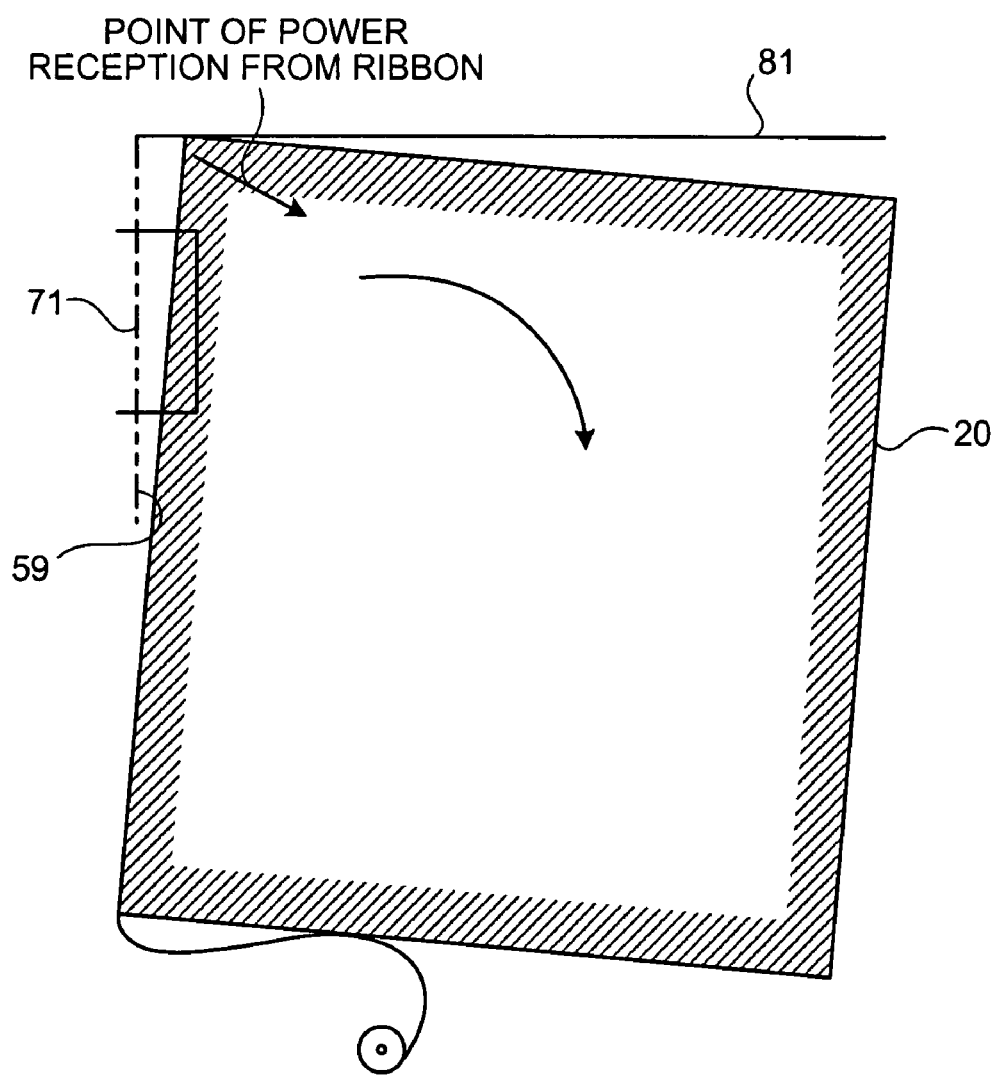
FIG. 14 is an explanatory diagram exaggeratingly illustrating a power reception point at which a corner on the tip side of the battery receives the power from the ribbon.

At the start of the operation of drawing the ribbon 81, as shown in FIG. 14, a corner on the front end side of the battery 20 corresponds to a power reception point at which the force from the ribbon 81 is received. There is the possibility such that the force of tilting the battery 20 to be ejected acts, and a trouble occurs among the peripheral members, particularly, between the battery-side connector 43 and the device-side connector 71 in the engaged state, and the battery 20 cannot be ejected. However, in the embodiment of the present invention, the battery 20 is allowed to move straight by the guide groove 44 and the rib 72, so that the battery 20 reliably moves in the ejecting direction without being tilted. When the ribbon 81 is drawn to a position at which the ribbon 81 is stretched between the slits 83 and 84 or its equivalent position, the battery rear end face 42c side goes out from the opening 53a, so that the battery 20 can be ejected.

Figure 15:
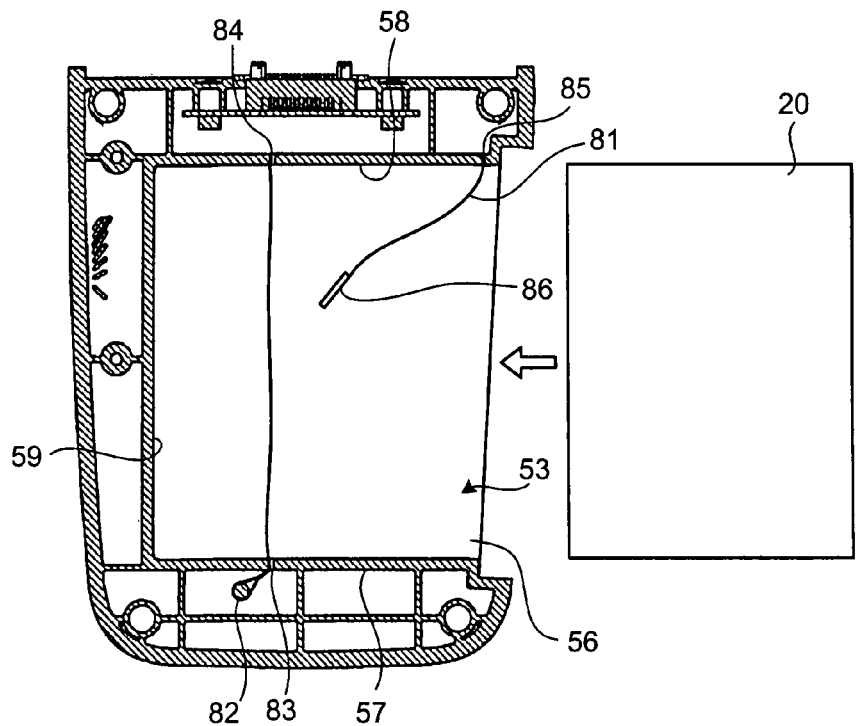
FIG. 15 is a horizontal cross section showing a state where the battery is inserted in a state where a tab exists in a battery housing.

The case of performing the operation of inserting the battery 20 in the state where the tab 86 portion exists in the battery housing 53 as shown in FIG. 15 will be described. In this case, when the operation of inserting the battery 20 is performed, since the tab 86 portion is thicker than the gap "d" between the battery 20 and the inner wall of the battery housing 53 and cannot pass through the gap "d", the tab 86 is pushed by the front end of the battery 20 to the deeper side.

Figure 16:
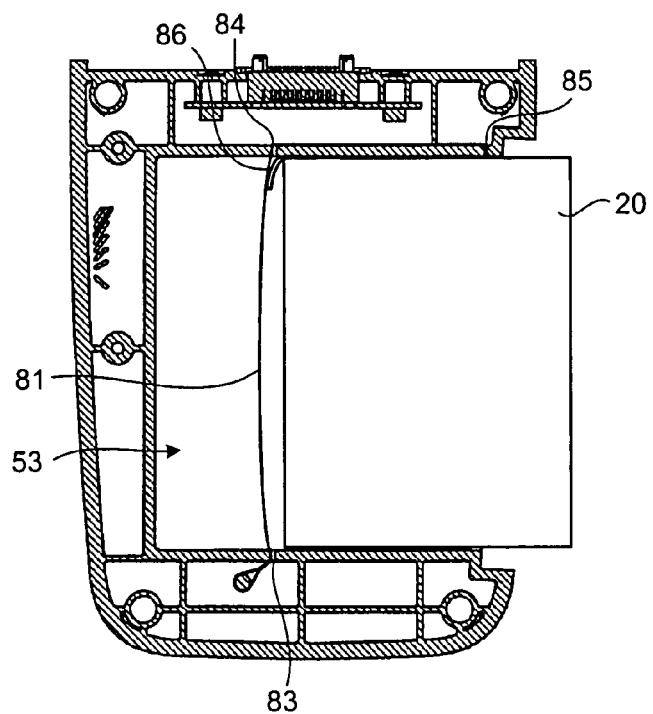
FIG. 16 is a horizontal cross section showing a state where a battery loading operation is disturbed by the tab.

However, routing of the ribbon 81 is performed by the slits 83 to 85, the ribbon 81 is set to be short as long as it does not disturb the ejecting operation, and the tab 86 is provided in a position in which the length from the slit 85 is shorter than the length in the insertion/detachment direction of the battery 20. Therefore, even when the tab 86 is pushed in by the battery 20, finally, as shown in FIG. 16, the ribbon 81 between the slit 85 and the tab 86 is stretched and the tab 86 cannot be pushed further. Thus, loading of the battery 20 such that the operation of loading the battery 20 to a normal position is disturbed by the tab 86, the battery 20 remains in an ejectable position, and the tab 86 enters can be prevented with reliability.

Figure 17:
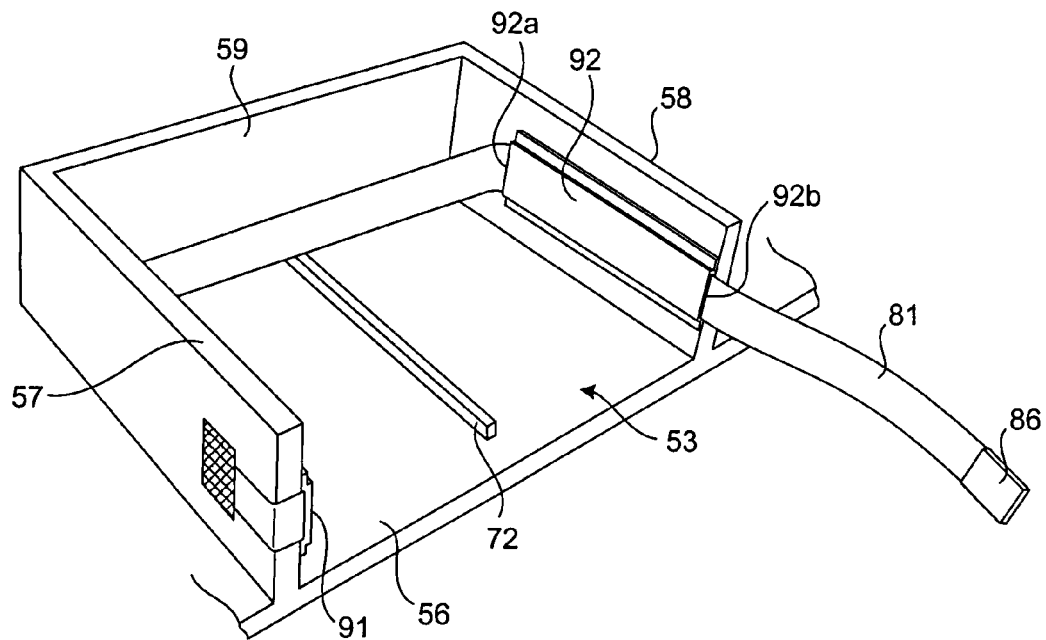
FIG. 17 is a schematic perspective view showing a first variant.

FIG. 17 is a perspective view showing a first variant in a simplified manner. In the first variant, guide members 91 and 92 forming a cylindrical path in which the ribbon 81 is inserted are provided by bonding or the like along the insertion direction of the battery 20 on the inside of the first and second side walls 57 and 58 forming the battery housing 53. A back-side end 92a of each of the guide members 91 and 92 (a back-side end of the guide member 91 is not shown) is set as a guide part. The fixed side of the ribbon 81 is routed via the guide member 91, routed to, for example, the outside of the side wall 57, and fixed on the outer face of the first side wall 57 by bonding or the like. A front-side end 92b of the guide member 92 serves as an outlet of the ribbon 81. The tab 86 has a three-dimensional shape, for example, a thick shape so that entrance to the cylindrical path of the guide member 92 from the front-side end 92b is not allowed. The guide members 91 and 92 may be formed by ribs provided upright in parallel with the first and second side walls 57 and 58 or partly formed in the insertion direction.

Figure 18:
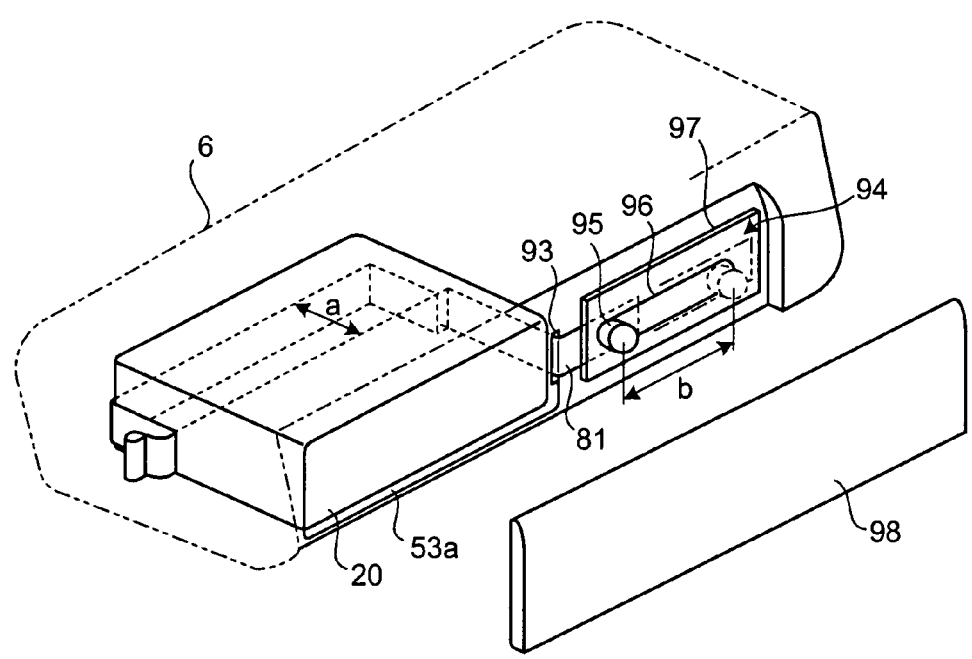
FIG. 18 is a schematic perspective view showing a second variant.

FIG. 18 is a perspective view showing a second variant in a simplified manner. In the second variant, in place of the slit 85, the outlet 93 of the ribbon 81 is formed in a part of the body case 51 on the side of the open 53a, and a slide drawing mechanism 94 for drawing the ribbon 81 is provided at the other end of the ribbon 81 which is drawn from the outlet 93. The slide drawing mechanism 94 is constructed by a slide knob 95 coupled to the other end of the ribbon 81, and a guide plate 97 having a long hole 96 specifying the operation direction and the operation amount of the slide knob 95. The length "b" of the long hole 96, that is, the operation amount of the slide knob 95 is set so as to satisfy the relation of b=2a where "a" denotes length from the contact face 59 to the position of the slits 83 and 84. A cover member 98 which can close the opening 53a and the slide drawing mechanism 94 is also provided.

FIG. 18 shows a state where the battery 20 is loaded. In the case of ejecting the battery 20, the cover member 98 is opened and, after that, the slide knob 95 is slid to the right as shown by an imaginary line. It makes the ribbon 81 move in the drawing direction, and the battery 20 in contact with the ribbon 81 also moves together to the opening 53a, so that the battery 20 can be taken out.

According to the second variant, the slide drawing mechanism 94 is coupled to the other end side of the ribbon 81, so that the other end side can be reliably prevented from being pulled into the ribbon insertion path or buried in the battery housing 53.

The present invention is not limited to the foregoing embodiments but can be variously modified without departing from the gist of the invention. For example, as the long member, a string member can be used in place of the band member such as the ribbon 81.

INDUSTRIAL APPLICABILITY

As described above, the portable electronic device and the capsule endoscope diagnosis system according to the invention are useful as a portable electronic device and a capsule endoscope diagnosis system having a battery housing in which a battery can be detachably housed and, more particularly, suitable for a portable electronic device and a capsule endoscope diagnosis system for taking out a housed battery by using a long material such as a ribbon.

The invention claimed is:

1. A capsule endoscope diagnosis system comprising:
a capsule endoscope which includes an image capturing unit, an illuminating unit capable of illuminating an image capturing region, and a transmitting unit capable of sending image data captured by the image capturing unit to the outside and can be swallowed by a subject;
a detector having an antenna structure attached to the body surface of the subject and receiving image data transmitted from the transmitting unit; and
a portable electronic device including:
a battery housing having, at one end of the battery housing, an opening to/from which a battery of a rectangular flat shape having two flat faces that are parallel to each other and a front end face that is perpendicular to the flat faces is allowed to be inserted/detached, and in which the battery is detachably housed;
a long member whose one end is fixed and which is routed in the battery housing, can be drawn by an operation of drawing the other end, and can be pushed to the deepest place in the insertion direction in the battery housing by an operation of inserting the battery whose battery front end face comes into contact with the long member;
guide parts provided on both side walls of the battery housing and, when the long member is drawn by the drawing operation, making the long member cross the battery housing so as to be stretched in a position where the battery can be taken out, wherein the portable electronic device is carried by the subject with the battery loaded in the battery housing, and stores the image data received by the detector; and
a device-side connector, to which a battery-side connector in the battery front end face can be inserted, in the deepest place in the insertion direction of the battery housing,
wherein the guide parts are provided in positions to set a position of contact, with the battery front end face, of the long member in the stretched state so that the long member does not come into contact with the battery-side connector.

2. The capsule endoscope diagnosis system according to claim 1, wherein the guide parts are provided in positions to make the long member cross the battery housing in a stretched state in a direction orthogonal to the insertion/detachment direction.

3. The capsule endoscope diagnosis system according to claim 1, wherein the guide parts are formed as slits which are formed in the side walls and in which the long member is inserted.

4. The capsule endoscope diagnosis system according to claim 1, wherein as the guide parts, back-side ends of guide members are used, the guide members being provided along an insertion direction on the side walls and in which the long member is inserted.

5. The capsule endoscope diagnosis system according to claim 1, further comprising an outlet which is provided at a position adjacent to the opening and from which the other end of the long member is insertably drawn to the outside, and
a three-dimensional tab, at the other end of the long member, whose entry to the outlet is restricted.

6. The capsule endoscope diagnosis system according to claim 5, wherein the tab has a three-dimensional shape larger than a gap between the battery and an inner face of the battery housing and provided in a position where length from the outlet is smaller than length in the insertion direction of the battery in the case where the long member is drawn at the maximum, and in the case where the tab exists in the battery housing, the tab interferes with an operation of loading the battery to a normal position.

7. The capsule endoscope diagnosis system according to claim 1, further comprising a cover member capable of closing the opening, wherein the tab can be housed in a space formed by a rear end face of the battery housed in the battery housing and the cover member.

8. The capsule endoscope diagnosis system according to claim 1, further comprising a slide drawing mechanism coupled to the other end of the long member and drawing the long member.

9. The capsule endoscope diagnosis system according to claim 8, further comprising a cover member capable of covering the opening and the slide drawing mechanism.

10. The capsule endoscope diagnosis system according to claim 1, further comprising an elastic member which is provided on a wall face in the insertion direction orthogonal to both side walls forming the battery housing, has biasing force by which the elastic member fits in a recess formed in an outer face of a loaded battery, and elastically fits in the recess.

11. The capsule endoscope diagnosis system according to claim 1, further comprising a rib which is provided on a wall face in the insertion direction orthogonal to both side walls forming the battery housing and slidably fits in a guide groove formed in an outer face of a battery and parallel with the insertion direction.

12. The capsule endoscope diagnosis system according to claim 1, wherein the long member is a band-shaped member.

* * * * *